US00PP10379P

United States Patent [19]

Adam, Jr.

[11] Patent Number: Plant 10,379

[45] Date of Patent: May 5, 1998

[54] PHILOX PLANT NAMED 'SHORTWOOD'

[76] Inventor: Sinclair A. Adam, Jr., 231 S. Bonsall Rd., Coatesville, Pa. 19320

[21] Appl. No.: 782,616

[22] Filed: Jan. 13, 1997

[51] Int. Cl.[6] ..... A01H 5/00

[52] U.S. Cl. ..... Plt./87.7

[58] Field of Search ..... Plt./87.7

*Primary Examiner*—James R. Feyrer
*Assistant Examiner*—Kent L. Bell
*Attorney, Agent, or Firm*—C. A. Whealy

[57] ABSTRACT

A distinctive cultivar of Phlox plant named 'Shortwood', characterized by its medium pink flower color with a dark hot pink center "eye"; resistance to Powdery Mildew; and long flowering period.

1 Drawing Sheet

The present invention relates to a new and distinct cultivar of Phlox, botanically known as *Phlox paniculata*, and hereinafter referred to by the cultivar name 'Shortwood'.

The new cultivar was selected by the inventor from seedling progeny from a cross of the *Phlox paniculata* cultivar 'Eva Cullem' (not patented) as the male or pollen parent with the *Phlox paniculata* cultivar 'David' (not patented) as the female or seed parent. The new cultivar was selected by the inventor at his nursey in Coatesville, Penna. from these seedlings.

In side-by-side comparisons in Coatesville, Penna., under commercial practice, plants of the new Phlox are different from plants of the male parent, the cultivar 'Eva Cullem' in the following characteristics:

1. Plants of the new Phlox are more resistant to Powdery Mildew than plants of the cultivar 'Eva Cullem'.
2. Plants of the new Phlox are taller than plants of the cultivar 'Eva Cullem'.
3. Plants of the new Phlox have smaller flowers, but are more freely flowering and flower for a longer period of time than plants of the cultivar 'Eva Cullem'.
4. Flowers of plants of the new Phlox are more fragrant than flowers of plants of the cultivar 'Eva Cullem'.

In addition to flower color, plants of the new Phlox differ from plants of the female parent, the cultivar 'David', in the following characteristics:

1. Plant of the new Phlox are more freely branching than plants of the cultivar 'David'.
2. Plants of the new Phlox flower for a longer period of time than plants of the cultivar 'David'.

Asexual reproduction of the new cultivar by tip cuttings taken at Coatesville, Penna., has shown that the unique features of this new Phlox plant are stable and reproduced true to type in successive generations of asexual reproduction.

The following traits have been repeatedly observed and are determined to be the unique characteristics of 'Shortwood'. These characteristics in combination distinguish the new Phlox plant as a new and distinct cultivar:

1. Medium pink flower color with a dark hot pink center "eye".
2. Resistance to Powdery Mildew.
3. Long flowering period, summer through fall.

The new Phlox plant has not been observed under all possible environmental conditions. The phenotype may vary significantly with variations in environment such as temperature, light level, nutrition and water status without, however, any variance in genotype.

The accompanying colored photographs illustrates the overall appearance of the new cultivar, showing the colors as true as it is reasonably possible to obtain in colored reproductions of this type.

The first photograph comprises a side perspective view of a typical plant of 'Shortwood'.

The second photograph comprises a close-up view of a typical flower of 'Shortwood'.

Flower and foliage colors in the photographs may appear different from the actual colors due to light reflectance.

The following observations, measurements, values, and comparisons dewcribe plants grown in Coatesville, Penna., in 1-gallon containers.

In the following description, color references are made to The Royal Horticultural Society Colour Chart except where general terms of ordinary dictionary significance are used.

Classification:

*Botanical.*—*Phlox paniculata* cultivar 'Shortwood'.

Parentage:

*Male or pollen parent.*—*Phlox paniculata* cv. 'Eva Cullem' (not patented).

*Female or seed parent.*—*Phlox paniculata* cv. 'David' (not patented).

Propagation:

*Type.*—By tip cuttings.

*Time to develop roots.*—Summer: 28 days at temperatures of 21° C. Winter: 40 days at temperatures of 20° C.

*Rooting habit.*—Vigorous, fibrous, and well-branched.

Plant description:

*Plant form and growth habit.*—Perennial, upright with lateral branches.

*Vigor.*—Moderate to vigorous.

*Branching habit.*—Freely branching.

*Height, soil level to top of flowers.*—75 to 90 cm.

*Stem description.*—Diameter: About 4 mm. Internode length: About 2.5 cm. Color: 146B. Texture: Glabrous.

Foliage description:

*Arrangement.*—Opposite, single.

*Leaf size, largest leaves.*—Length: About 13 cm. Width: About 4 cm.

*Leaf shape.*—Linear, lanceolate.

*Leaf apex.*—Acuminate.

*Leaf base.*—Truncate.

*Margin type.*—Entire, undulating.

*Texture.*—Smooth, glabrous.

*Color.*—Young foliage, adaxial surface: Darker than 146A. Young foliage, abaxial surface: 147B. Mature foliage, adaxial surface: Darker than 146A. Mature foliage, abaxial surface: 147B. Venation, adaxial surface: 146A. Venation, abaxial surface: 146B.

*Petiole.*—Length: About 5 mm. Diameter: About 2.5 mm. Color: 146C.

*Durability of foliage to stress.*—Good.

Flower description:

*Natural flowering season.*—Summer through fall, usually in the Northern Hemisphere, from July through October.

*Flower arrangement.*—Flowers arranged in panicles with usually six flowers forming at every axil, flowers face upward and outward. Freely flowering.

*Flower appearance.*—Trumpet with fused corolla with five that petals. Medium pink petals with dark hot pink center "eye". Not persistent, self-cleaning.

*Fragrance.*—Sweet.

*Flower diameter.*—About 2.75 cm.

*Flower depth (height).*—About 2.5 cm.

*Flower bud.*—Length: About 1.5 cm. Diameter: About 5 mm. Shape: Ovoid. Color: 75A/77C.

*Petals.*—Appearance: Satiny. Texture: Smooth. Arrangement: Trumpet with five petals fused into a corolla tube. Shape: Rounded. Margin: Entire. Surface: Usually flat, edges may be slightly curved upwards. Size: Length: About 1.3 cm. Width: About 1.2 cm. Color: When opening, adaxial surface: 77B. When opening, adaxial surface: 75A. Fully opened, adaxial surface: Darker than 75A with overtones of 77B and streaks of white. Base, 57A, forming a dark hot pink center "eye". Fully opened, abaxial surface: Darker than 75A with overtones of 77B and streaks of white. Throat (inside surface): 75A. Tube (outside surface): 75A. Petal color fading to: 75B.

*Sepals/calyx.*—Appearance: Five sepals fused into a narrow calyx tube. Sepal texture: Thin, smooth. Sepal shape: Linear. Sepal apex: Very pointed. Sepal color: 146B. Calyx length: About 8 mm. Calyx diameter: About 2 mm.

*Peduncles.*—Length: About 5 mm. Angle: Straight. Strength: Strong. Color: 146B with red overtones.

*Reproductive organs.*—Androecium: Stamen number: Five. Anther shape: Narrowly oblong. Anther size: About 2 mm. Amount of pollen: Moderate. Pollen color: 5D. Gynoecium: Pistil number: One. Pistil length: About 1.7 cm. Stigma shape: Rounded. Stigma color: Whitish green. Style length: About 1.5 cm. Style color: Whitish green. Ovary color: Green, 144A.

Disease resistance: Under commercial conditions, good resistance to Powdery Mildew has been observed.

Seed production: Seed production is rarely observed.

It is claimed:

1. A new and distinct Phlox plant named 'Shortwood', as illustrated and described.

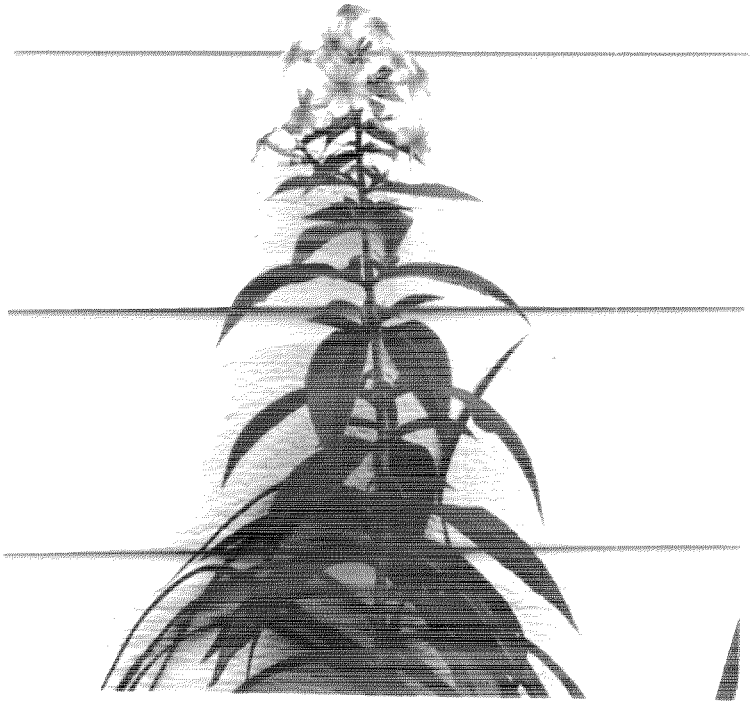
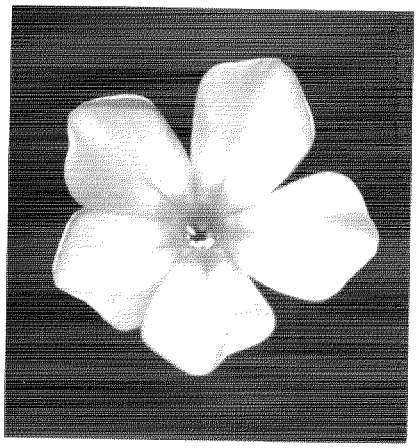

* * * * *